United States Patent [19]

Barbone

[11] Patent Number: 5,073,110
[45] Date of Patent: Dec. 17, 1991

[54] ARTICULATING BALL COPING AND ASSOCIATED DEVICES

[75] Inventor: Noram K. Barbone, Mansfield, Ohio

[73] Assignee: Implant Plastics Corporation, Mansfield, Ohio

[21] Appl. No.: 527,002

[22] Filed: May 21, 1990

[51] Int. Cl.$^5$ .............................................. A61C 8/00
[52] U.S. Cl. ................................................... 433/173
[58] Field of Search ................ 433/173, 174, 175, 176

[56] References Cited

U.S. PATENT DOCUMENTS

| | | | |
|---|---|---|---|
| 3,579,831 | 5/1971 | Stevens | 433/174 |
| 3,656,236 | 4/1972 | Kurer | 433/174 X |
| 3,732,621 | 5/1973 | Bostrom | 433/174 |
| 4,431,416 | 2/1984 | Niznick | 433/174 |
| 4,568,216 | 2/1986 | Mizusawa | 403/122 X |
| 4,645,453 | 2/1987 | Niznick | 433/173 |
| 4,679,958 | 7/1987 | Mizusawa | 403/122 X |
| 4,682,951 | 7/1987 | Linkow | 433/173 |
| 4,713,004 | 12/1987 | Linkow et al. | 433/174 |
| 4,793,808 | 12/1988 | Kirsch | 433/173 |
| 4,832,601 | 5/1989 | Linden | 433/173 |
| 4,854,874 | 8/1989 | Neuwirth | 433/176 |
| 4,907,969 | 3/1990 | Ward | 433/174 X |

FOREIGN PATENT DOCUMENTS 0106815 4/1984 European Pat. Off. ............ 433/173

Primary Examiner—Robert P. Swiatek
Assistant Examiner—Nicholas D. Lucchesi
Attorney, Agent, or Firm—Fay, Sharpe, Beall, Fagan, Minnich & McKee

[57] ABSTRACT

A coping insert adapted for use with an endosseous dental implant anchoring element includes a shaft for insertion into an opening in the anchoring element and a head end for engaging and supporting a dental prosthesis. The insert is molded entirely of a resinous plastic and the head end and the shaft constitute separate elements joined by a ball and socket type joint for allowing angular positioning of the head end relative to the shaft. The ball and socket type joint include cooperating surfaces which can be bonded together when the head end has been positioned in a predetermined position relative to the shaft. The socket element portion also includes a pin element for allowing axial adjustment of the head element relative to the shaft element.

6 Claims, 3 Drawing Sheets

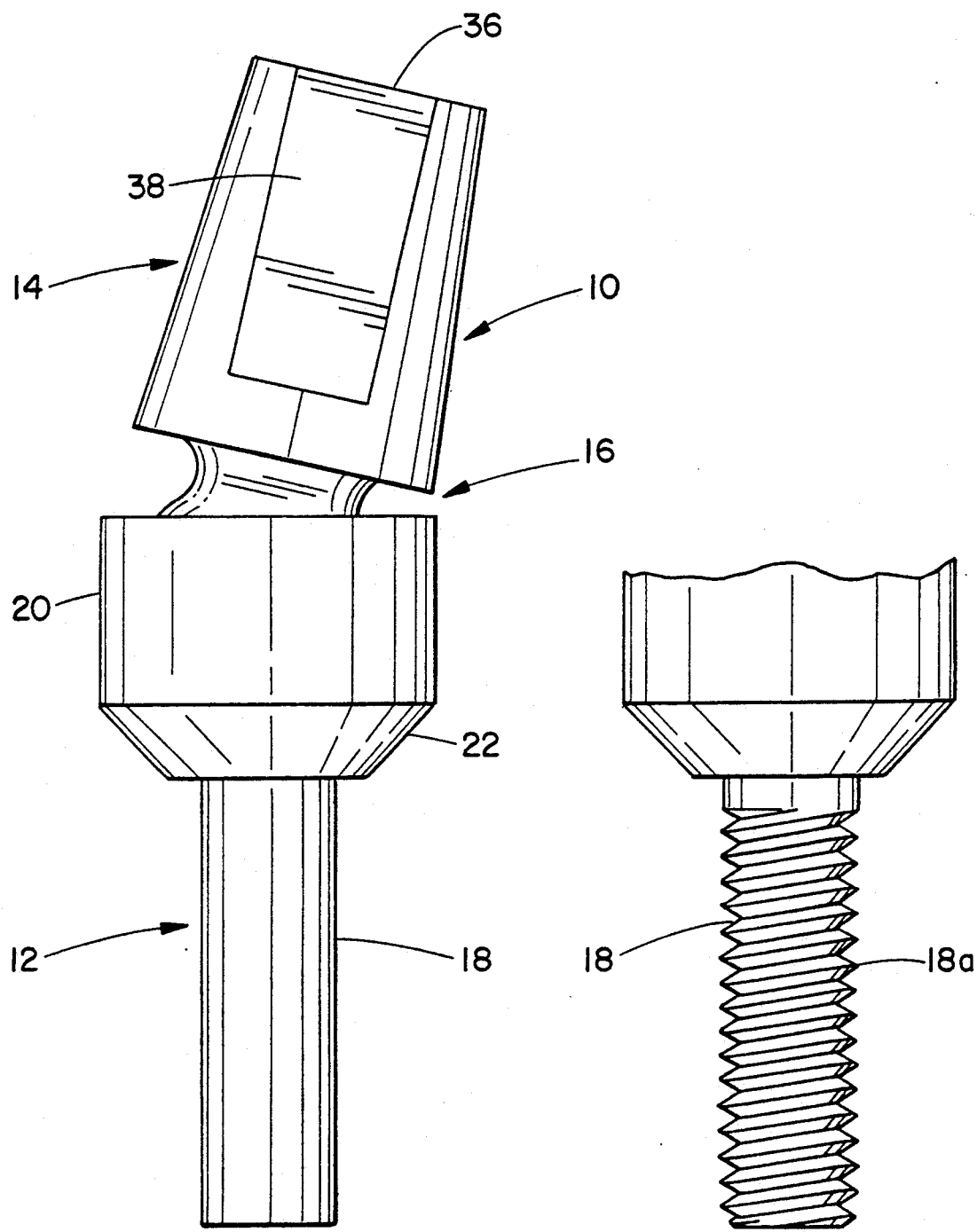
FIG. 1　　　FIG. IA

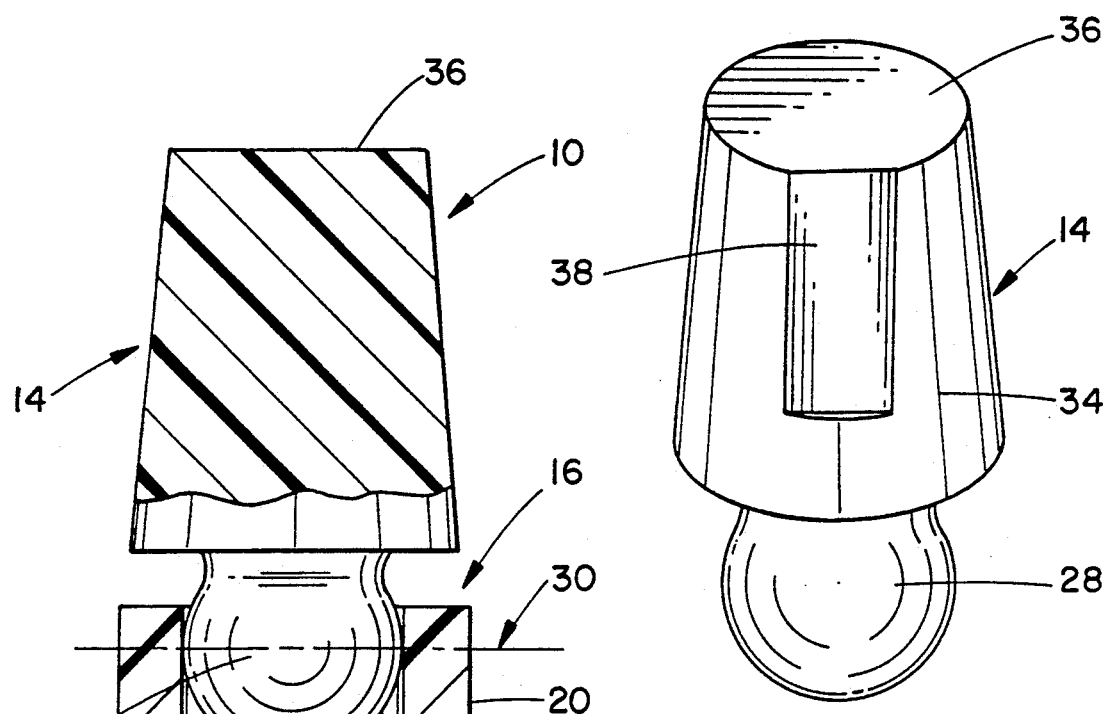
FIG. 3
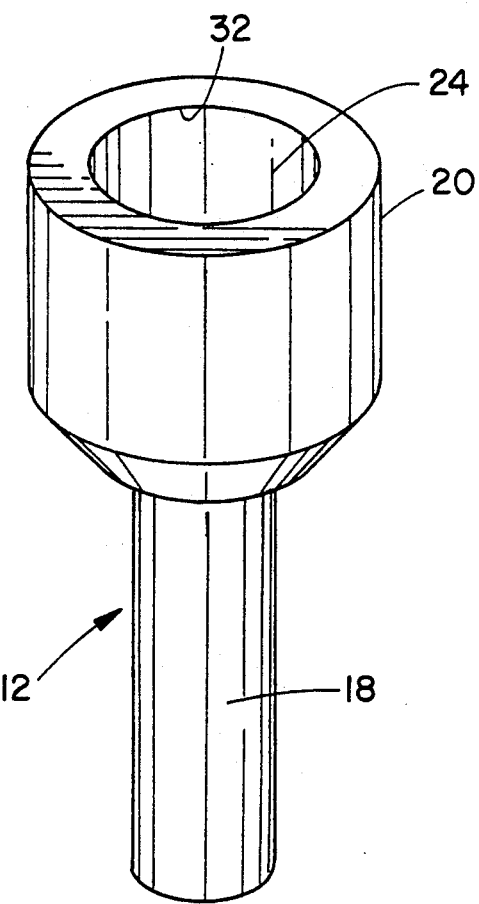
FIG. 2
FIG. 4

5,073,110

ARTICULATING BALL COPING AND ASSOCIATED DEVICES

BACKGROUND OF THE INVENTION

The subject invention is directed toward the art of dental devices and appliances and, more particularly, to articles for facilitating the manufacture or formation of dental implant attachment structures.

During the formation of support structure for mounting or insertion in dental implant anchoring means for the purpose of holding prosthetic teeth, it is generally required to form a precise pattern of the necessary support structure. The pattern is then used for direct or indirect molding of the support structure in a high strength material.

The process of forming the patterns is generally quite difficult and time consuming and involves installing coping inserts into the attachment elements implanted in the alveolar bone. These coping inserts must be positioned and angularly adjusted to assume the necessary orientation for properly receiving the prosthetic tooth or teeth. Typically, adjustment has required repeated removal and replacement of the coping insert together with cutting, grinding and/or bending.

The subject invention overcomes the above noted problems and provides a coping insert which can be readily adjusted throughout a wide range of angular orientations.

SUMMARY OF THE INVENTION

In accordance with the present invention, there is provided a coping insert of the type adapted for use with an endosseous dental implant anchoring means. The insert includes a shaft means, either threaded or straight, for insertion into an opening in the anchoring means and a head end for engaging and supporting a dental prosthesis. Accordingly to the invention, the coping insert includes the improvement wherein the insert is molded entirely of a resinous plastic and the head end and shaft means constitute separate elements joined by a ball and socket type joint for allowing angular positioning of the head end relative to the shaft means. The ball and socket type joint includes cooperating surfaces which frictionally engage to allow the head end and the shaft means to be positioned in predetermined relative relationships and maintained in those relationships until they are permanently bonded through the use of an adhesive or the like.

Preferably, and in accordance with a more limited aspect of the invention, the ball and socket type joint comprises an axially inwardly extending socket molded in one of the elements and a ball molded on the other of the elements. Preferably, the socket includes an axially extending pin section formed at the base thereof and extending axially for engaging and locating the ball axially in the socket.

As can readily be seen, the combination of the molded ball and socket elements allows final positioning and adjustment of the components to be carried out rapidly and without cutting, grinding, or bending of the coping insert. When the positioning is complete, the two elements can be bonded together such as through the use of a drop of solvent type adhesive or the like.

After the insert has been formed to its desired shape and bonded in the desired angular relationship, it can then used for molding directly or indirectly a metal component which can be placed directly into the endosseous dental implant anchoring means for supporting a dental prosthesis.

In accordance with a still further object of the invention, the pin of the socket has a relatively small diameter and is spaced from the side walls of the socket an amount sufficient to allow ready access to the end of the pin for removal of portions thereof so that the length of the pin can be adjusted for final axial positioning of the head end relative to the shaft means.

As can be seen from the foregoing, a primary object of the invention is the provision of a molded plastic coping insert as a two-part, relatively adjustable structure which can be quickly adjusted to the desired final angular relationship and bonded in the desired position.

Yet another object of the invention is the provision of a coping insert of the general type described wherein the relative axial positioning between the head end and the shaft means can be easily adjusted before the elements are bonded in their final desired relationship.

A still further object of the invention is the provision of a coping insert of the type described wherein the base element can be used as a separate element apart from the head and ball end thereof.

A still further object is the provision of a coping insert of the type under consideration wherein the elements are adapted for use in either directly or indirectly molding metal duplicates for supporting and attaching dental prostheses to endosseous dental implant anchoring means.

BRIEF DESCRIPTION OF THE DRAWINGS

The above and other objects and advantages will become apparent from the following description when read in conjunction with the accompanying drawings wherein:

FIG. 1 is a greatly enlarged side elevational view of a coping insert formed in accordance with a preferred embodiment of the subject invention;

FIG. 1A is a showing of a modified form of the shaft end of the insert;

FIG. 2 is a cross-sectional view taken on line 2—2 of FIG. 1;

FIGS. 3 and 4 are pictorial views of the head and shaft or base end portions, respectively, of the insert of FIG. 1 prior to the time that the elements have been assembled into the FIG. 1 arrangement; and, FIG. 5 is an exploded view of a structure incorporating a threaded insert between the head and base portions.

DETAILED DESCRIPTION OF THE PREFERRED EMBODIMENT

Figure 5:
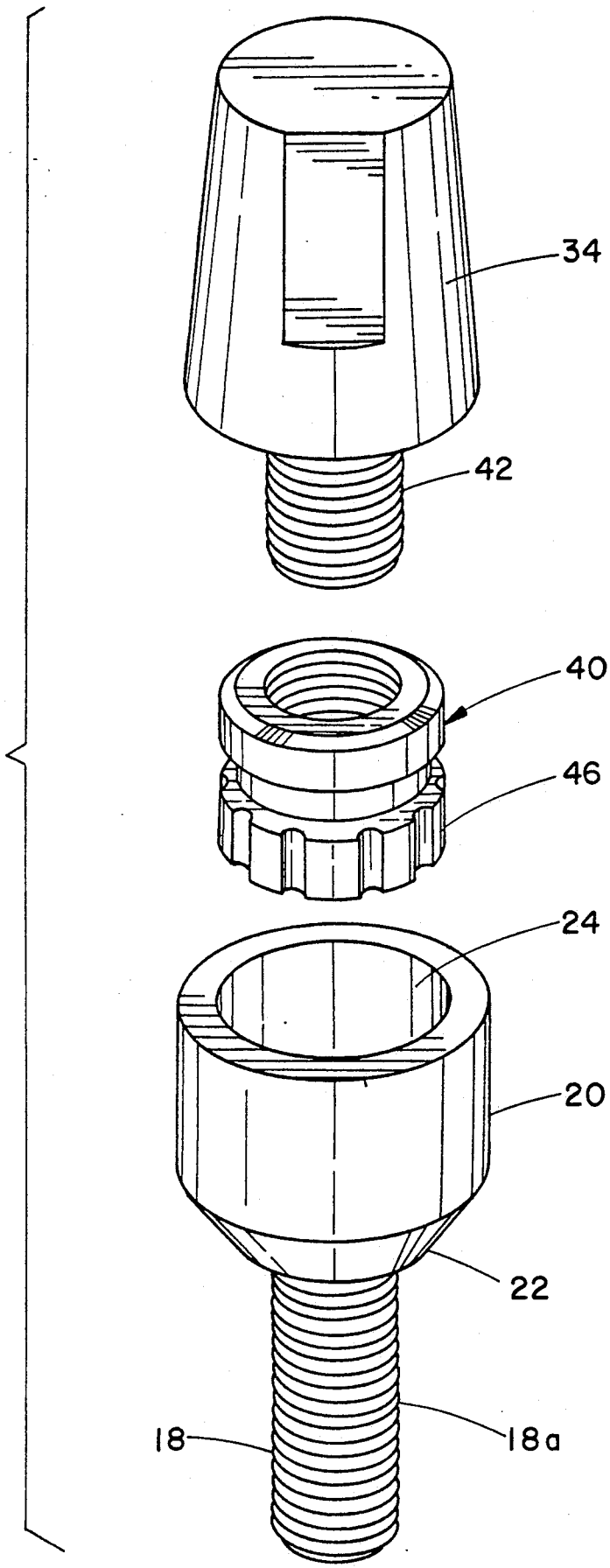

Referring more particularly the drawings wherein the showings are for the purpose of illustrating a preferred embodiment of the invention only, and not for the purpose of limiting same, FIG. 1 shows the overall assembled arrangement of a coping insert formed in accordance with the invention and designated generally with the reference numeral 10. The insert 10 is illustrated as including a shaft means or base element 12 and a head end or support element 14. Each of the elements 12 and 14 are molded from a suitable resinous material, such as nylon or other plastic having suitable characteristics. The two elements are formed entirely separately and are joined by a ball and socket type connecting arrangement indicated generally by the reference numeral 16.

In the embodiment under consideration, the shaft means or base element 12 includes a elongated shaft or connecting end portion 18 which has a cylindrical configuration and is integrally joined with an enlarged upper end 20. The upper end 20 is axially aligned with the shaft portion 18 and has a generally cylindrical configuration as illustrated. Preferably, the lower end of the portion 20 is chamfered as shown at 22.

The shaft 18 is sized and of a length to fit suitably within the usual shaft receiving opening or passage in the endosseous dental implant anchoring means (not shown in FIG. 1). As is apparent and well known, the shaft 18 can be provided with preformed helical threads 18a to mate with the threads typically found in the implant anchoring means. Such threads are illustrated in FIG. 1A.

As best illustrated in FIGS. 2 and 4, the upper end 20 of the shaft means or base element 12 is provided with an axially inwardly extending cylindrical socket 24 which is axially aligned with the shaft 18. For reasons which will subsequently be described at some length, a short shaft or pin 26 is preferably molded integrally with the element 12 at the base of socket 24 as illustrated in FIG. 2.

The socket 24 is sized and arranged to closely receive a ball element 28 formed integrally with the head or support element 14. As particularly shown in FIG. 2, the diameter of the ball 28 is selected so as to be substantially equal to the open interior diameter of the socket portion 24. Additionally, the diameter of the ball 28 is related to the upper end of the socket 24 and the pin 26 so that the uppermost end of the head end portion 20 is above the mid-line or center 30 of the ball member 28. Additionally, it is preferred that the outer end of the head end 20 have a relatively narrow axially extending circumferential wall portion 32 formed thereabout. Preferably, the wall portion 32 is permanently deflected radially inward to a diameter less than the diameter of the ball member 28. Thus, a frictional engagement takes place between the socket and the ball member to allow relative arcuate positioning of the head end 14 relative to the base element 12 to be accomplished as desired. That is, the head end portion 14 can be angularly adjusted relative to the base portion. Additionally, it should be noted that the head end portion could have a variety of different configurations but is shown generally having a frusto conical main body 34 which terminates in a flat upper wall 36. This is a desirable and conventional shape for receiving and holding a dental prosthesis. Additionally, as best illustrated in FIG. 3, the body portion 34 preferably includes a flat 38 which acts to position or prevent rotation of a dental prosthesis joined thereto.

In assembling the head end element 14 to the base or shaft element 12, the pin 26 can be adjusted in length through a grinding or cutting operation to vary the axial length or extent of the head end from the socket end 20. When the two elements are properly in engagement and in the desired position of axial and angular adjustment, a drop of suitable adhesive or the like at the groove or juncture between the ball and socket element will cause the two elements to be bonded into the desired preset and adjusted relationship. Thereafter, the joined elements can be removed from their position within the patient's mouth and used for molding a permanent metal supporting element to be replaced in the patient's mouth for mounting the necessary dental prostheses.

Although the subject coping insert can be used substantially without any bending, grinding, or cutting, it should be appreciated that such shaping can be carried out if necessary. For example, suitable screw receiving tapped openings can be formed into the body portion 34 if necessary.

It should also be noted that the base or socket end 20 can be used for other types of prosthesis elements and the like. In this regard, FIG. 5 illustrates in exploded perspective view an embodiment wherein the ball portion or member is constituted by a separate member 40 which is arranged to be received in socket portion 24 for tilting adjustment therein. In this embodiment, the member 40 is formed of metal and is internally threaded as shown to receive a threaded shaft 42 on the main body 34'. The groove lower rim 46 of member 40 acts to assist in holding member 40 in its adjusted position. Through known casting techniques, the member 40 can be cast in the duplicate of base or socket end 20 to provide a threaded opening in the resulting casting.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

What is claimed is:

1. In a copying insert adapted for use with an endosseous dental implant anchoring means including shaft means for insertion into an opening in said anchoring means and a head end for engaging and supporting a dental prosthesis the improvement wherein said insert is molded entirely of a resinous plastic and said head end and said shaft means constitute separate elements joined by a ball and socket type joint for allowing angular positioning of said head end relative to said shaft means, said socket of said joint including adjustment means in the form of an elongated member molded in the interior of said socket to extend axially thereof for allowing axial adjustment and positioning of said ball therein by cutting the elongated member to a desired length.

2. The copying insert as defined in claim 1 wherein said ball and socket type joint comprises an axially inwardly extending socket molded in one of said elements and a ball molded on the other of said elements and said adjustment means comprises a pin element formed in the base of said socket.

3. The coping insert as defined in claim 2 wherein said pin element is formed in said socket in axial alignment with said socket.

4. The coping insert as defined in claim 3 wherein said socket is cylindrical and formed in said element which carries said shaft means, said shaft means having a central axis which is coaxial with said cylindrical socket.

5. The coping insert as defined in claim 4 wherein said shaft means is cylindrical.

6. The coping insert as defined in claim 4 wherein said shaft means is provided with helical screw threads.

* * * * *